United States Patent [19]
Brown et al.

[11] Patent Number: 6,127,596
[45] Date of Patent: Oct. 3, 2000

[54] IMPLANTABLE ORTHOPEDIC PROSTHESIS HAVING TISSUE ATTACHMENT SURFACE AND METHOD OF MANUFACTURE

[75] Inventors: Steve Brown, Pflugerville; John Wheeler; Mark Lester, both of Austin; James Burrows, Cedar Park, all of Tex.

[73] Assignee: Sulzer Orthopedics Inc., Austin, Tex.

[21] Appl. No.: 09/012,199

[22] Filed: Jan. 23, 1998

[51] Int. Cl.⁷ ................................ A61F 2/28; A61F 2/32
[52] U.S. Cl. .................................................. 623/16; 623/22
[58] Field of Search .................................. 623/16, 22, 18; 606/61, 69, 70

[56] References Cited

U.S. PATENT DOCUMENTS

| | | | |
|---|---|---|---|
| 3,605,123 | 9/1971 | Hahn | 3/1 |
| 4,363,627 | 12/1982 | Windeler | 433/167 |
| 4,536,894 | 8/1985 | Galante et al. | 623/22 |
| 4,608,052 | 8/1986 | Van Kampen et al. | 623/22 |
| 4,659,331 | 4/1987 | Matthews et al. | 623/20 |
| 4,673,409 | 6/1987 | Van Kampen | 623/23 |
| 4,718,915 | 1/1988 | Epinette | 623/23 |
| 4,778,469 | 10/1988 | Lin et al. | 623/16 |
| 4,904,263 | 2/1990 | Buechel et al. | 623/18 |
| 4,904,348 | 2/1990 | Domes et al. | 204/4 |
| 4,944,759 | 7/1990 | Mallory et al. | 623/22 |
| 4,988,351 | 1/1991 | Paulos et al. | 606/72 |
| 5,018,285 | 5/1991 | Zolman et al. | 29/465 |
| 5,108,395 | 4/1992 | Laurain | 606/61 |
| 5,108,432 | 4/1992 | Gustavson | 623/16 |
| 5,108,435 | 4/1992 | Gustavson et al. | 623/16 |
| 5,201,766 | 4/1993 | Georgette | 623/16 |
| 5,246,530 | 9/1993 | Bugle et al. | 156/643 |
| 5,326,354 | 7/1994 | Kwarteng | 623/66 |
| 5,344,421 | 9/1994 | Crook | 606/61 |
| 5,373,621 | 12/1994 | Ducheyne et al. | 29/527.2 |
| 5,522,894 | 6/1996 | Draenert | 623/16 |
| 5,531,793 | 7/1996 | Kelman et al. | 623/16 |
| 5,607,607 | 3/1997 | Naiman et al. | 219/121.68 |
| 5,658,349 | 8/1997 | Brooks et al. | 623/23 |
| 5,681,310 | 10/1997 | Yuan et al. | 606/61 |
| 5,690,843 | 11/1997 | Schmitt et al. | 219/69.17 |

FOREIGN PATENT DOCUMENTS

| | | |
|---|---|---|
| 0 162 604 | 11/1985 | European Pat. Off. . |
| 0 269 256 | 6/1988 | European Pat. Off. . |
| 0 407 332 | 1/1991 | European Pat. Off. . |
| 0 515 056 A1 | 11/1992 | European Pat. Off. . |
| 34 06 358 | 12/1984 | Germany . |
| 40 31 520 | 4/1992 | Germany . |
| 195 24 221 A1 | 1/1997 | Germany . |
| WO 97/36708 | 10/1997 | WIPO . |

*Primary Examiner*—Paul J. Hirsch
*Assistant Examiner*—Michael B. Priddy
*Attorney, Agent, or Firm*—Philip S. Lyren; Kenneth S. Barrow

[57] ABSTRACT

An implantable orthopedic prosthesis has a macro/microtextured bone and soft tissue attachment surface to which a spiked washer is clamped by a threaded bolt received through said washer and threaded into said prosthesis. Soft tissue is secured to the prosthesis by clamping between said washer and said soft tissue attachment surface. The tissue attachment surface is arranged as a regular grid of depressions separated by orthogonal ridges formed by electrodischarge machining of the prosthesis using a machining electrode having a mold-opposite surface texture with a microtextured roughened surface finish. The spacing of the spikes is and integer multiple of the spacing of the depressions to assure registry of the spikes with the depressions.

8 Claims, 3 Drawing Sheets

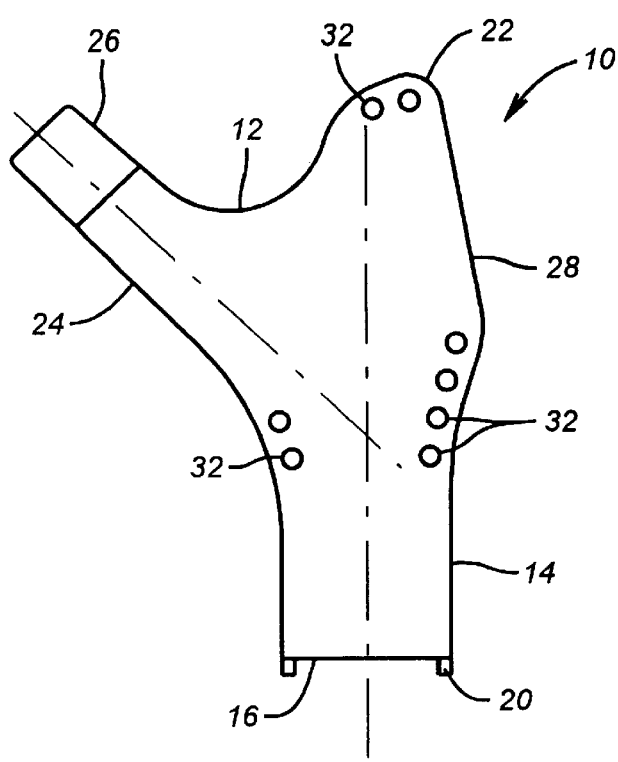
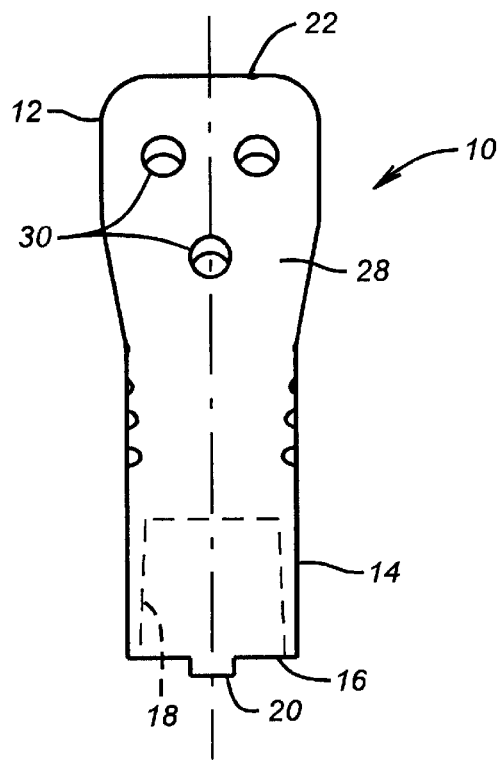
FIG. 1   FIG. 2
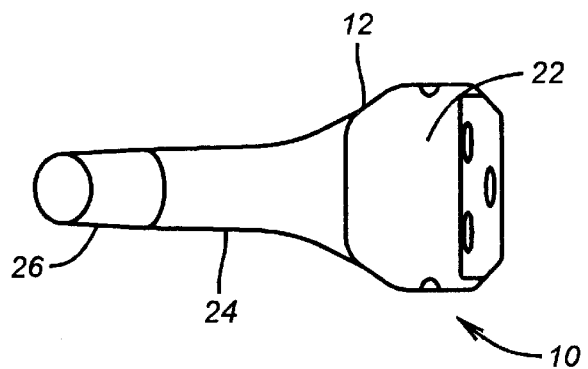
FIG. 3

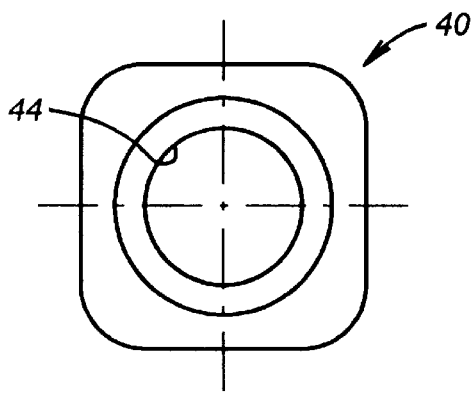
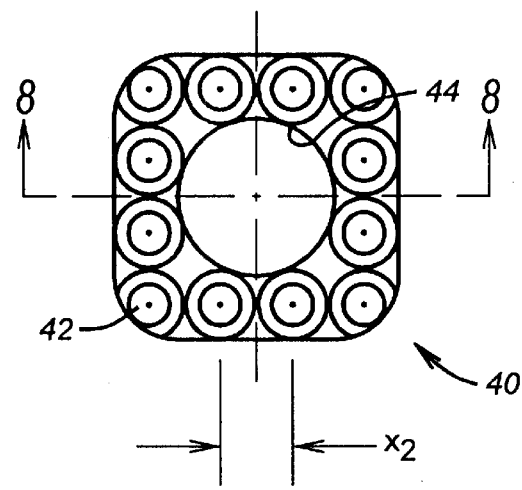
FIG. 6
FIG. 7
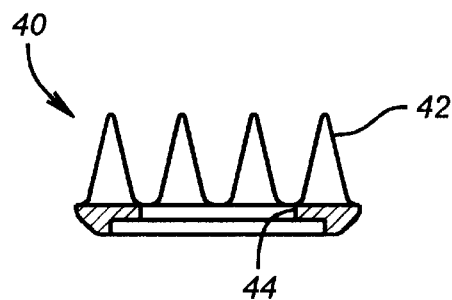
FIG. 8
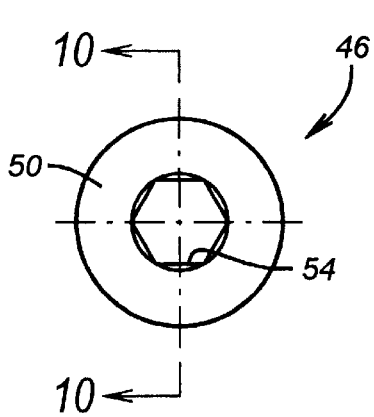
FIG. 9
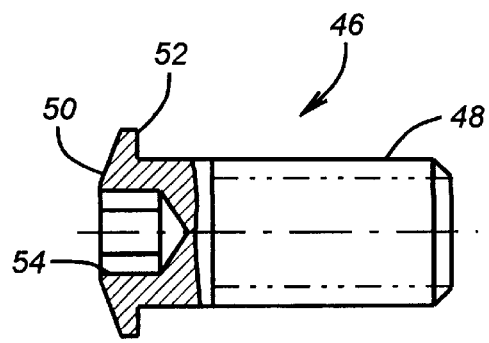
FIG. 10

IMPLANTABLE ORTHOPEDIC PROSTHESIS HAVING TISSUE ATTACHMENT SURFACE AND METHOD OF MANUFACTURE

BACKGROUND OF THE INVENTION

1. Field of the Invention

This invention is generally related to implantable orthopedic prostheses and methods for their manufacture, and is more particularly related to textured surfaces on implantable orthopedic prostheses for accepting ingrowth and ongrowth of bone and soft tissue, and to methods for manufacturing such textured surfaces.

2. Background Information

Implantable orthopedic prostheses, in one form, comprise manufactured replacements for the ends and articulating surfaces of the bones of the skeleton. Such prostheses are implanted to repair or reconstruct all or part of an articulating skeletal joint that is functioning abnormally due to disease, trauma or congenital defect. Before implanting such prostheses, the defective natural articulating surfaces must be removed by resecting the terminal portion of the affected bone. Ordinarily, it is desirable that the smallest possible amount of bone be removed, consistent with providing a sound resected bony surface to which the prosthesis can be affixed and which can provide good structural support for the prosthesis. Ligaments and other soft tissues that are important to the functioning of the joint are preserved to the maximum possible extent. Typically, the surgical resection of the bone is sufficiently conservative that the areas of the bone to which ligaments and tendons attach are not disturbed.

Other forms of implantable orthopedic prostheses, beyond providing manufactured replacements for the ends and articulating surfaces of the bones of the skeletal joints, also provide manufactured replacements for portions of the bones distant from the articulating surface. These other forms may be used in cases of abnormally extensive atrophy or resorption of bone in the vicinity of the articulating surface or prior implant, or in cases where an extensive amount of bone is to be intentionally resected to treat oncological or other diseases of the bone. Because the natural bony areas to which ligaments, tendons and other soft tissues attach are often lost to such extensive resections of the bone, implantable orthopedic implants designed for such cases often include means for attaching bone and/or soft tissue directly to the implant. It is desirable that such means provide an initial mechanical attachment, supplemented by later ingrowth and ongrowth of the bone and soft tissue to the prosthesis. This and other desirable advantages are achieved by the present invention.

SUMMARY OF THE INVENTION

According to one aspect of the invention, a method of manufacturing an implantable orthopedic prosthesis having a macro/micro-textured bone and soft tissue-attachment surface, comprising the following steps. An implantable orthopedic prosthesis having an electrically conductive surface is provided. An electrodischarge machining electrode having a surface that is contoured in a mold-opposite configuration to a desired macro-textured bone ingrowth attachment surface is provided. The contoured machining electrode is placed adjacent the electrically conductive surface of the implantable orthopedic prosthesis. Electrical energy is caused to discharge between the machining electrode and the implantable orthopedic prosthesis to effect EDM machining of the electrically conductive surface to generate the desired macro-textured bone ingrowth attachment surface on the implantable orthopedic prosthesis.

According to another aspect of the invention, an implantable orthopedic prosthesis having a macro/micro-textured bone and soft tissue-attachment surface includes an implantable orthopedic prosthetic body having a micro-textured soft tissue ongrowth attachment surface thereon. The micro-textured surface is a roughened surface texture covering the macro-texturing for optimizing soft tissue ongrowth. A washer has spikes for engaging the macro-textured tissue-attachment surface. Means are provided for retaining the washer in engagement with the implantable prosthetic body such that the spikes engage the macro-textured tissue attachment surface under pressure. The macro-textured tissue-attachment surface has a regular pattern of texture and the washer has the spikes arrayed in a similarly regular pattern such that registry of the spikes with the textured surface is assured.

BRIEF DESCRIPTION OF THE DRAWINGS

FIG. 1 is an anterior elevational view of an implantable orthopedic prosthesis constructed in accordance with the present invention.

FIG. 2 is a lateral elevational view of the implantable orthopedic prosthesis of FIG. 1.

FIG. 3 is a top view of the implantable orthopedic prosthesis of FIG. 1.

FIG. 6 is a top view of a soft tissue affixation washer for use with the implantable orthopedic prosthesis of FIG. 1.

FIG. 7 is a bottom view of the soft tissue affixation washer of FIG. 6.

FIG. 8 is a cross-sectional view of the soft tissue affixation washer of FIG. 6, taken in plane 8—8 of FIG. 7 and viewed in the direction of the arrows.

FIG. 9 is a axial view of a threaded bolt for use with the affixation washer of FIG. 6 and the implantable orthopedic prosthesis of FIG. 1.

FIG. 10 is a longitudinal sectional view of the threaded bolt of FIG. 9, taken in plane 10—10 of FIG. 9 and viewed in the direction of the arrows.

DETAILED DESCRIPTION OF THE PREFERRED EMBODIMENT

Figure 4:
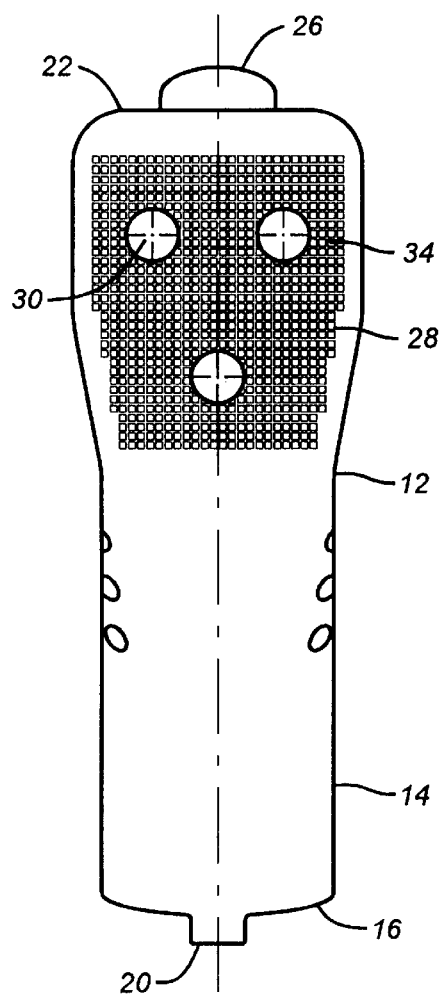
FIG. 4 is an enlarged lateral view of the implantable orthopedic prosthesis of FIG. 1, particularly showing a soft tissue ingrowth surface thereon.

Referring particularly to FIGS. 1–3, an implantable orthopedic prosthesis 10 is shown that is constructed according to the present invention. The illustrated embodiment of prosthesis 10 comprises a proximal body component 12 of a hip joint portion of a modular femoral prosthesis system designed for oncology patients. When fitted with an appropriate distal member (not shown) and a femoral head prosthesis (not shown), the proximal body 12 can replace a substantial portion of the proximal femur, including bony structures such as the greater and lesser trochanters and calcar femorale that are not resected during conventional implantation of a hip joint prosthesis, but are often resected in treatment of femoral bone cancers. Proximal body 12 includes a distal shank 14 having a distal end 16 in which is recessed a female conical taper 18 open at distal end 16. Female conical taper 16, also known as a Morse taper, is designed to receive and frictionally interlock with a corresponding male taper of a distal member (not shown) of the modular femoral prosthesis system. A pair of diametrically opposed keys 20 extend axially from distal end 16 and are designed to be received in corresponding notches in a proximal shoulder of the distal member to prevent relative rotation between proximal body 12 and the distal member. Proximal body 12 also includes a proximal trochanter portion 22 and a medial neck 24 that replace corresponding portions of the natural femur. Neck 24 terminates in a male conical taper 26, or Morse taper, designed to be received within and frictionally interlock with a corresponding female taper of a femoral head prosthesis (not shown) of the modular femoral prosthesis system. A lateral surface 28 of trochanter portion 22 includes three blind, threaded bores 30 disposed within a macro-textured soft tissue attachment surface of lateral surface 28 which is described further below with regard to FIGS. 4 and 5. A plurality of suture holes 32 are disposed at the lateral-anterior, lateral-posterior, medial-anterior, medial-posterior and superior aspects of proximal body 12 for receiving sutures or cerclage wires used to secure soft tissues to proximal body 12 or to stabilize bone or bone grafts to proximal body 12.

Figure 5:
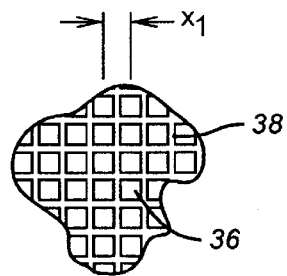
FIG. 5 is a magnified view of a portion of the soft tissue ingrowth surface of FIG. 4.

With particular reference to FIGS. 4 and 5, lateral trochanter surface 28 of proximal body 12 includes a macro/micro-textured soft tissue attachment surface 34 interrupted by blind, threaded bores 30. As shown best in FIG. 5, tissue attachment surface 34 comprises a grid pattern of depressions 36 separated by orthogonally disposed ridges 38. The tops of ridges 38 are disposed at the same general elevation as that of surrounding lateral trochanter surface 28, whereas the bottoms of depressions 36 are disposed at a lower elevation. As preferred, depressions 36 are formed in relatively smooth lateral surface 28 by removing material at discrete grid locations, leaving behind ridges 38. The resulting macro/textured surface 34 resembles the well-known surface configuration of a waffle. Depressions 36, as preferred, are generally square with rounded corners as viewed in plan. The side walls of depressions 36, which also constitute the side walls of ridges 38, generally taper from the tops of ridges 38 inwardly toward the center of each depression 36. Depressions 36 are arranged on a center-to-center spacing "$x_1$" of about 0.040 inches, as preferred. Depressions 36 have a maximum depth of about 0.030 inches below the general elevation of the tops of ridges 38, as preferred.

Referring to FIGS. 6–8, a soft tissue affixation washer 40 is shown. Washer 40 cooperates with tissue attachment surface 34 to provide initial mechanical fixation of soft tissue to proximal body 12. Washer 40 includes a plurality of elongate conical spikes 42 extending perpendicularly from the bottom surface of washer 40. In use, washer 40 is disposed adjacent surface 34 of proximal body 12 such that spikes 42 point toward surface 34, with soft tissue such as a tendon clamped. Spikes 42 are substantially evenly spaced in a grid pattern interrupted by a circular through-hole 44 disposed in the center of washer 40. Spikes 42 are arranged on a center-to-center spacing "$x_2$" that is an integer multiple of the spacing dimension "$x_1$" of the depressions 36 of surface 34. Consequently, when washer 40 is disposed adjacent surface 34, complete registry of all of the spikes 42 within the depressions 36 is assured.

Now referring to FIGS. 9 and 19, a bolt 46 is shown that is useful in combination with the above-described washer 40 and macro-textured surface 34. Bolt 46 includes an externally threaded shank 48 and a head 50 having an annular shoulder 52. Head 50 also includes an axial recess 54 having a hexagonal sidewall for receiving a tool for imparting torque to bolt 46. The shank 48 and annular shoulder 52 are sized such that shank 48 can pass through hole 44 of washer 40 and be threadedly received within blind, threaded hole 30 of proximal body 12, with shoulder 52 bearing on the top surface of washer 40. By tightening bolt 46 in threaded hole 30 with washer 40 disposed beneath head 50, the soft tissue disposed between spikes 42 and surface 34 is effectively clamped to proximal body 12. Later, the soft tissue eventually grows into or onto surface 34 to effect an attachment of even greater security.

Figure 11:
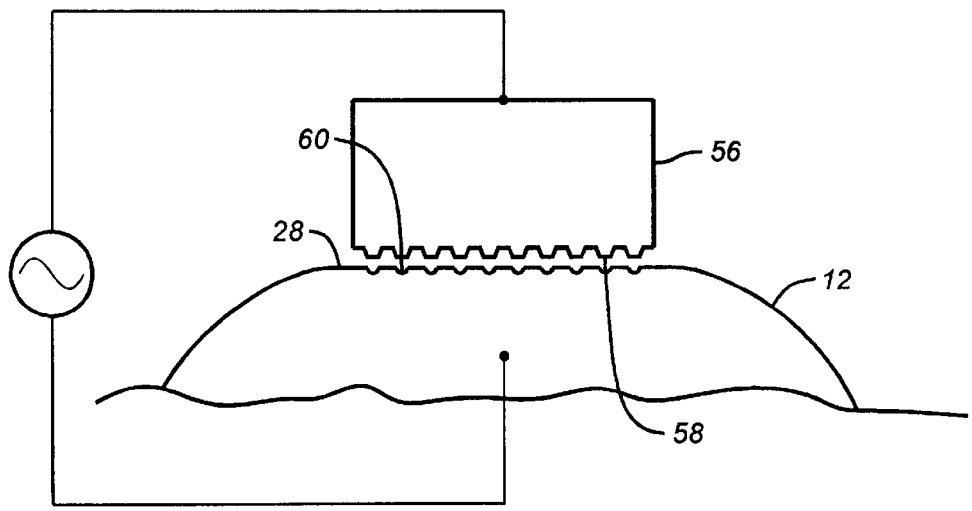
FIG. 11 is a schematic representation of an electrodischarge machining process, in accordance with the present invention, for forming the tissue ingrowth surface of FIG. 4.

Referring to FIG. 11, a method of manufacturing the macro-textured tissue attachment surface is described. According to the present invention, the macrotextured tissue attachment surface 34 is formed by by the process of electrospark or electrodischarge machining, also known as EDM. In this process, an electrode tool 56 formed in the shape of the desired surface texture comprises one electrode and the workpiece, proximal body 12, comprises the other electrode of a spark gap. Electrical potential is applied across the spark gap in a manner well known in the art of EDM, causing electrical discharges between the shaped electrode tool and the workpiece. This causes the surface of the workpiece to be eroded into a mold-opposite copy of the electrode tool. Consequently, the preferred EDM electrode is shaped complementarily to the contour of tissue attachment surface 34, much like a waffle iron is shaped complementarily to the resulting surface contour of a waffle. More particularly, the electrode tool has an array of high points 58 arranged in a grid pattern, the high points corresponding to the depressions 36 to be machined in lateral trochanter surface 28. During EDM, electrical sparks jump between the high points of the electrode tool and the surface 28, causing pits 60 to be electrically eroded in surface 28. Those pits eventually enlarge as EDM continues until the pits reach the desired size and shape of depressions 36.

The present invention has been illustrated and described with particularity in terms of a preferred embodiment and preferred method of manufacture. Nevertheless, it should be understood that no limitation of the scope of the invention is intended. The scope of the invention is defined by the claims appended hereto. It should also be understood that variations of the particular embodiments described herein incorporating the principles of the invention will occur to those of ordinary skill in the art and yet be within the scope of the appended claims.

We claim:

1. An implantable orthopedic femoral prosthesis for replacing a proximal femur and connecting to soft tissue of a patient, comprising:

an implantable orthopedic prosthetic body having a distal shank portion, a medial neck portion, and a proximal trochanter portion having a macro-textured tissue attachment surface thereon;

a washer having spikes adapted to clamp the soft tissue against said macro-textured tissue-attachment surface; and means for retaining said washer in engagement with said implantable prosthetic body such that said spikes engage said macro-textured tissue attachment surface under pressure;

said macro-textured tissue-attachment surface having a regular pattern of texture and said washer having said spikes arrayed in a similarly regular pattern such that registry of said spikes with said textured surface is assured.

2. The prosthesis of claim 1, in which said regular pattern of texture comprises a substantially regular grid.

3. The prosthesis of claim 2, in which said regular grid has depressions spaced at regular intervals.

4. The prosthesis of claim 3, in which said spikes are spaced at intervals that are integer multiples of the regular intervals at which said depressions are spaced.

5. The prosthesis of claim 1 in which the spikes have an elongated conical configuration.

6. The prosthesis of claim 1 in which the macro-textured tissue attachment surface has depressions with a maximum depth of about 0.030 inches.

7. A method for attaching soft tissue of a patient to an implantable orthopedic femoral prosthesis, comprising the steps of:

providing an implantable orthopedic femoral prosthesis having a body with a distal shank portion, a medial neck portion, and a proximal trochanter portion having a macro-textured tissue attachment surface with a pattern of texture;

providing a washer having a plurality of projections with a pattern of texture similar to the pattern of texture of the macro-textured tissue attachment surface;

implanting the orthopedic femoral prosthesis at the proximal end of the femur of the patient;

positioning the soft tissue of the patient between the projections and the macro-textured tissue attachment surface of the trochanter portion; and tightening the washer against the trochanter portion to clamp the soft tissue between the projections and the macro-textured tissue attachment surface.

8. The method of claim 7 further comprising the step of maintaining the washer against the trochanter portion while the soft tissue grows into the macro-textured tissue attachment surface.

* * * * *